United States Patent [19]

Waite

[11] Patent Number: 5,574,134
[45] Date of Patent: Nov. 12, 1996

[54] POLYPEPTIDE MONOMERS, LINEARLY EXTENDED AND/OR CROSSLINKED FORMS THEREOF, AND APPLICATIONS THEREOF

[75] Inventor: J. Herbert Waite, Lewes, Del.

[73] Assignee: University of Delaware, Newark, Del.

[21] Appl. No.: 839,745

[22] Filed: Feb. 19, 1992

Related U.S. Application Data

[63] Continuation of Ser. No. 378,599, Jul. 11, 1989, abandoned.

[51] Int. Cl.$^6$ ............................................. A61K 38/04
[52] U.S. Cl. .............................................. 530/328; 530/331
[58] Field of Search ................................. 530/331, 328

[56] References Cited

U.S. PATENT DOCUMENTS

| | | | |
|---|---|---|---|
| 4,496,397 | 1/1985 | Waite | 530/328 |
| 4,585,585 | 4/1986 | Waite | 530/328 |
| 4,687,740 | 8/1987 | Waite | 435/68.1 |
| 4,746,731 | 5/1988 | Bohn et al. | 530/350 |
| 4,748,156 | 5/1988 | Aoki et al. | 530/350 |
| 4,755,460 | 7/1988 | Bostwick et al. | 530/350 |
| 4,777,241 | 10/1988 | Irikura et al. | 530/350 |
| 4,780,529 | 10/1988 | Hao | 530/350 |
| 4,808,702 | 2/1989 | Waite | 530/328 |
| 4,853,220 | 8/1989 | Clemmensen et al. | 530/350 |
| 4,882,425 | 11/1989 | Hull et al. | 530/350 |
| 4,897,464 | 1/1990 | Vallee et al. | 530/350 |
| 4,946,943 | 8/1990 | Bloch | 530/377 |
| 5,015,677 | 5/1991 | Benedict et al. | 530/328 |
| 5,037,958 | 8/1991 | Hashimoto et al. | 530/350 |
| 5,049,504 | 9/1991 | Maugh et al. | 530/350 |
| 5,108,923 | 4/1992 | Benedict et al. | 435/240.1 |

OTHER PUBLICATIONS

Waite, J. H., J. Biol. Chem, 258, 2911–2915 (1983).
Waite, J. H. et al, Science 212, 1038–1043 (1981).
Waite, J. H. et al, Meth. in Enzymol. 107, 397–413 (1984).
Brown, C. H., Quart. J. Microsc. Sci. 93, 487–502 (1952).
Waite, J. H., Int. J. Adhesion and Adhesives 7, 9–14 (1987).
Comyn, J., Ch. 8 in Developments in Adhesives (Kinlock, A. J., ed.), vol. 2, Applied Sci. Pub., Barking, UK, 1981, pp. 279–313.
Pierpont, C. G. et al, Coord. Chem. Rev. 38, 45–87 (1981).
Waite, J. H., J. Mar. Biol. Ass. UK 65, 359–371 (1985).
Waite, J. H. J. Comp. Physiol. B 156, 491–496 (1986).

Primary Examiner—James J. Seidleck
Assistant Examiner—T. Mosley
Attorney, Agent, or Firm—Connolly & Hutz

[57] ABSTRACT

A water-resistant polyphenolic protein adhesive has been obtained from the Atlantic ribbed mussel, *Geukensia (Modiolus) demissa*. This protein provides a natural model for synthetic or bioengineered adhesives and is characterized by a Gly-Tyr-Lys or, more frequently, Gly-Dop-Lys "tail" fragment of a repeating octapeptide or nonapeptide unit. A complete octapeptide or nonapeptide unit (including both the 5- or 6-amino acid residue "head" as well as the 3-residue "tail") can be represented as follows:

$$[Gln|Glu]_x\text{-Thr/Ala-Gly-Dop/Tyr-}Y^1\text{-}Y^2\text{-Gly-Tyr/Dop-Lys}$$

where x is zero or one, $Y^1$ is Val, Leu, Asp or Ser, and $Y^2$ is Ala, Pro, Hyp, or Leu.

The tripeptide "tail" and/or the 5- or 6-residue "head" of the polypeptide is useful as a single unit (curable with difunctional crosslinkers or the like) or as a repeating unit.

12 Claims, No Drawings

POLYPEPTIDE MONOMERS, LINEARLY EXTENDED AND/OR CROSSLINKED FORMS THEREOF, AND APPLICATIONS THEREOF

This invention was made with United States government support awarded by the National Science Foundation (NSF), grant no. DMB 8500301 and the Office of Naval Research, grant no. N00014-86K-0717, and the National Institues of Health, grant no. DE-08058-02. The United States government has certain rights in this invention.

This application is a continuation of U.S. patent application Ser. No. 07/378,599 filed on Jul. 11, 1989, now abandoned.

BACKGROUND OF THE INVENTION

1. Field of the Invention

This invention relates to polypeptides, i.e. chains of amino acids generally linked via peptide bonds. An aspect of this invention relates to polypeptide monomers or prepolymers containing up to nine amino acid units and chain-extended and/or crosslinked polymers of high molecular weight derived from these monomers or prepolymers. Another aspect of this invention relates to polypeptides having adhesive properties which can be cured at moderate temperatures in the presence of water or biological fluids, the curing mechanism involving either a self-cure or the introduction of an accelerator and/or a crosslinking agent. Still another aspect of this invention relates to the resulting crosslinked polypeptides and adhesive bonds obtained from them. Further aspects of this invention relate to two-part adhesive systems comprising polypeptides (part A) and a crosslinking agent or accelerator therefor (part B) and methods for using such adhesive systems in biological systems, where they are biocompatible, and in applications requiring a water-resistant adhesive bond which is biodegradable. Still another aspect of this invention relates to "hybrid" polymers having a conventional synthetic polymer backbone and amino acid sequences linked to this backbone.

DESCRIPTION OF THE PRIOR ART

It has long been known that polypeptides in the form of proteins can be used in adhesive compositions. Traditional examples of protein adhesives include fish glue and horse glue.

Recently, it has been discovered that there are relatively more exotic biological sources for adhesive compositions. Polyphenolic proteins have been isolated from the mussel genus Mytilus and have been described by Waite et al, *Science* 212, 1038 (1981). Indeed, several species of common marine mussels are known to have the ability to secure themselves to solid substrates through a complex array of plaque-tipped collagenous byssal threads, an important capability of these sea creatures which enables them to resist being dislodged by wave movements and the like. The ends of the byssal threads are rich in the polyphenolic adhesive substance, and the mussel mixes the adhesive with a curing enzyme (phenoloxidase) and a mucosubstance to provide a complex 3-component natural adhesive system. Needless to say, this adhesive system must be capable of curing at moderate temperatures (i.e. ambient sea water temperatures) and in the presence of water.

Even more recently, it has been discovered that an adhesive system can be formulated along the lines of the natural model occurring in the genus Mytilus by focusing in on a relatively low molecular weight polypeptide having a ten-acid sequence. Instead of a rather large polypeptide chain having a molecular weight of about 110,000 to 140,000, one can discern a relatively small number of amino acid residues which account for about 80% of all the amino acid residues within the polypeptide and which appear in a decapeptide sequence. This decapeptide sequence is repeated many times in the long-chain polypeptide and is considered to be the key to the highly useful properties observed in nature and adaptable to medical applications requiring a degree of biocompatibility. See U.S. Pat. Nos. 4,496,397 (Waite), issued Jan. 29, 1985 and 4,585,585 (Waite), issued Apr. 29, 1986.

In addition to the relative simplicity of the decapeptide sequence (as compared to the large polypeptides having molecular weights in excess of 100,000), other significant features of the decapeptide adhesives of Waite include lysine and tyrosine or 3,4-dihydroxyphenylalanine residues which provide potential crosslinking sites. Further interesting features include an unusually frequent appearance of proline or hydroxyproline residues and an essentially complete absence of glycine residues. Stated another way, this decapeptide sequence is not typical of connective tissue proteins such as collagens.

For a detailed discussion of the characterization of the 10 amino acid sequence discovered in the rather large polypeptide chains obtained from the common mussel *Mytilus edulis*, see Waite, J. Biological Chem. 258, 2911–2915 (1983).

The species *Mytilus edulis* and *Mytilus californianus*, which by now have been studied fairly extensively, are not the only marine organisms which have evolved elaborate adhesive mechanisms which allow them to attach to a wide variety of surfaces under water. However, it is presently believed that these are the only species which have been investigated from the standpoint of providing natural models for the type of polyphenolic, water-resistant, bioadhesive systems described in U.S. Pat. No. 4,585,585. The decapeptide which is essentially the basis for these bioadhesives can be chain-extended into a large molecule possessing the adhesive capabilities of the naturally-occurring bioadhesive proteins by linking together up to 1000 decapeptide repeating units. The repeating units can be linked to each other by peptide linkages, either directly (head-tail), using classical methods of protein synthesis, or by amino acid or oligopeptide linking groups or other compounds reactive with amine groups or carboxyl groups. Alternatively, these decapeptides can be linked together with aldehydes or, more preferably, dialdehydes and other bifunctional compounds which can react with groups pendent from the decapeptide chain, thereby introducing a degree of crosslinking. In addition to dialdehydes, other suitable bifunctional groups include imido esters, diisocyanates, and the like. Potential crosslinking sites on the decapeptide molecule include pendent phenolic groups and pendent aliphatic primary amino groups.

SUMMARY OF THE INVENTION

A quite different and rather unusual natural model for adhesive systems has now been discovered, i.e. the adhesive protein produced by the Atlantic ribbed mussel *Geukensia (Modiolus) demissa*. This marine organism has also evolved an elaborate adhesive mechanism involving secretion of extraorganismic tendons (byssus threads) which adhere by way of an adhesive plaque onto available surfaces in the aquatic environment. Another point in common with the two *Mytilus* species investigated in the prior art is the ability to provide an adhesive molecule which competes with and resists the subversive action of water. However, although the Atlantic ribbed mussel is a Mytilid like the two previously studied mussels, it is dramatically different in its primary choice of habitat. Whereas *M. edulis* and *M. californianus* are both exposed to waves in the high-energy intertidal zone, *G. demissa* commonly lives with at least two thirds of its body buried in the sulfide-rich mud of intertidal salt marshes where it is attached by way of its byssus threads to the rhyzomes of cord grass. With a thermal range of −22° to 40° C. and a salinity range of at least 0°–70°/00, the ribbed mussel is particularly impressive for its physiological and biochemical tolerance.

Surprisingly, many features of the *G. demissa* proteinaceous adhesive are chemically quite distinct from the large polypeptides produced by the two previously studied *Mytilus* species. Despite some similarities in amino acid composition (e.g. high levels of dihydroxyphenylalanine and lysine), one of the most abundant amino acid residues in the Atlantic ribbed mussel adhesive is glycine, somewhat along the lines of a collagen, though not quite as plentiful as the glycine in collagen. Proline and hydroxyproline levels are lower in the Atlantic ribbed mussel adhesive as compared to the *M. edulis* and *M. californianus* adhesives.

The new sequences of this invention (which are derived from or based upon the Atlantic ribbed mussel adhesive) are considered to be advantageous in their low level of post-translational modifications, smaller percentage of proline units, and lower isoelectric points as compared to many known non-collagen sequences.

One of these novel sequences is based upon tripeptide fragments which occur with great frequency in the naturally-occurring adhesive. Other novel sequences include octapeptides and nonapeptides described below.

The tripeptide fragments can be represented by formula I, set forth below:

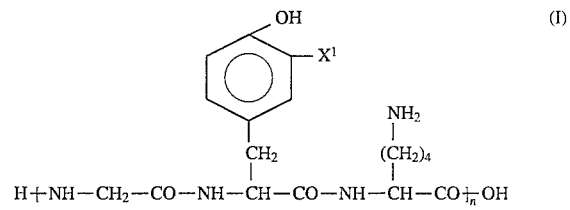

in which $X^1$ is H or OH, and n is a number from 1 to 1000, e.g. 1 to 100. Salts, including internal salts, are considered to be within the scope of Formula I. In the preferred tripeptides, $X^1$ is OH and n is greater than 1, e.g. up to about 10 or 20. When $X^1$=OH, the tripeptide can also be represented by Formula:

$$\text{Gly-Dop-Lys} \qquad \text{(Ia)}$$

wherein Gly is a glycine residue, Dop is a dihydroxyphenylalanine residue, and Lys is a lysine residue.

Preferred octapeptides and nonapeptides are represented by Formula II:

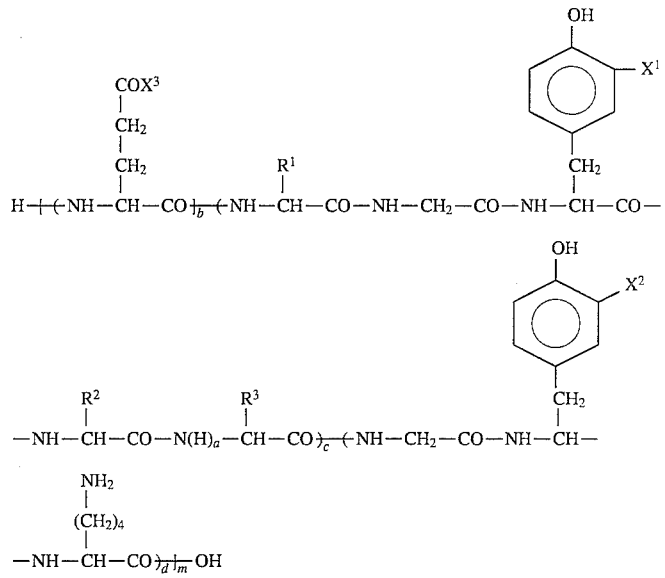

in which $X^1$ and $X^2$ are the same or different and are H or OH;

$X^3$ is OH or $NH_2$;

$R^1$, $R^2$, and $R^3$ are the same or different and are H; —$CH_3$;

where $R^4$ is H or —$CH_3$; —$CH_2COOH$; —$CH(CH_3)_2$; or —$CH_2CH(CH_3)_2$; and $R^3$, together with the C-atom on which it is substituted and the N-atom adjacent thereto, can be a 5-member heterocycle of the formula

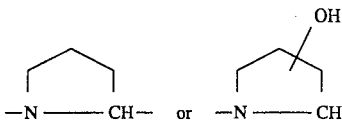

where the OH is in the 3- or 4- position;

a is 1, except when $R^3$ is part of said 5-member heterocycle, in which case a is zero;

b is zero or 1, b being zero in the case of the octapeptides and b being 1 in the case of the nonapeptides;

c is a number from 1 to 1000, and is preferably 1;

d is a number from 0 to 1000 and is preferably 1; and m is a number from 1 to 1000, preferably up to 20, more preferably up to 10;

the numbers a through d being selected independently of each other.

The polypeptides of formula II can be considered to include salts, e.g. internal salts, wherein a proton is transfered from a terminal —COOH to a terminal —$NH_2$, as in a Zwitterion.

The polypeptides described above can be chain-extended (linked head/tail) by classical polypeptide synthesis techniques or can be crosslinked, e.g. through hydroxyphenyl or dihydroxyphenyl groups of tyrosine or dihydroxyphenylalanine residues or through pendant aliphatic amine groups, e.g. the —$(CH_2)_4NH_2$ group of a lysine residue. Moreover, these polypeptides can be linked to the backbone of a conventional synthetic polymer (e.g. polyacrylic or polymethacrylic acid, poly[alkylenemine], etc.) to impart biocompatibility or biodegradability to an otherwise biologically inert or incompatible material.

When utilized as adhesives, either in a biological or an industrial context, the polypeptides of this invention can be self-cured and/or cured with the aid of a crosslinking agent and/or an accelerator, and conventional two-part formulation techniques can be used to provide a rapidly-curable adhesive system in a conveniently useable form.

Adhesives of this invention are more biocompatible for medical and dental uses, e.g. as wound closure adhesives, than are curable acrylate monomer adhesives; moreover, they tend to generate less heat during curing. In an industrial context, adhesives of this invention are biodegradable, even after they have been fully cured. Even if microorganisms or naturally-occurring enzymes are unable to "recognize" the amino acid sequence of the cured adhesive, various microorganisms in the environment have a much greater ability to break the peptide (—CO—NH—) linkages of these polypeptides than the linkages occurring in totally synthetic adhesives such as the acrylates, urethanes, phenol-aldehydes, etc. Accordingly, even if a period of years is required to break down the cured polypeptide adhesive, the rate of biodegration will still be faster than many of the commonly-used synthetic adhesives.

DETAILED DESCRIPTION

As noted previously, marine mussels have evolved elaborate adhesive mechanisms that allow them to attach to a wide variety of hard surfaces in an aquatic environment. The mechanism of adhesive bonding to these hard surfaces permits a strong bond to be formed, notwithstanding the presence of water and considerable motion (waves, tides, and the like), and the bond can last for days, weeks, or even months under these very adverse conditions. The adhesive bonds are not permanent; however, the degradation of the bond over a long period of time provides a desirable model of behavior for adhesives used in an industrial context (where biodegradability is useful) and in a medical context (where, for example, a wound closure bond is gradually replaced by the formation of adherent scar tissue, rendering the original adhesive bond superfluous). Another interesting and useful aspect of the natural adhesive model is that the monomer, so to speak, which becomes cured to form an extremely high molecular weight polypeptide is itself a large and complex molecule, so that the curing of this natural "monomer" generates very little heat of reaction. In a medical context (e.g. in the closing of wounds with an adhesive material), it has been fairly common in the past to use relatively small monomeric compounds which generate a considerable amount of heat of reaction upon polymerization. The amount of heat thus formed can be large enough to pose risks to the patient.

The natural mechanism used by marine mussels to attach themselves to a surface have been studied at least since 1952. See, for example, C. H. Brown, *Quart. J. Microsc. Sci.* 93, 487–502 (1952). It has been found that the marine mussels secrete extraorganismic tendons called byssus threads that "originate" in the byssus retractor muscles and adhere by way of an adhesive plaque onto available hard surfaces in the environment. Permanent attachment in a marine environment is a challenging physical and chemical problem which has been solved by the mussels through the biosynthesis of unusual adhesive molecules which can compete with and resist the subversive action of water. See J. Waite, *Int. J. Adhesion Adhesives*, 7, 9–14 (1987); J. Comyn, in *Developments in Adhesives* (Kinloch, A. J., ed.), Vol. 2, Applied Science Publishers, Barking, U. K., 1981, pages 279–313. The adhesive proteins of two intertidal mussels of the species *Mytilus* have been studied in depth and discussed previously, and the rather unusually frequent appearance of lysine (Lys), tyrosine (Tyr) and 3,4-dihydroxyphenylalanine (Dop or DOPA) residues has been pointed out. The o-diphenolic DOPA side chain is believed to be ideally suited to chemibsorption by the chelation of surface metals in mineral or metallic substrata (Pierpont et al, *Coord. Chem. Rev.* 38, 45–87 [1981]; Kummert et al, *J. Colliod Interf. Sci.* 75, 373–385 [1980]); in fact, it is not uncommon for the o-diphenolic moiety to form organometallic complexes with Fe(III), Al(III), Si(IV) and similar complexes having stability constants that exceed $10^{30}$ at the pH of sea water. Terminal carboxylic acid and amino groups (particularly the $C_4$-aliphatic primary amino group of lysine) can also participate in chemical reactions which are believed to have a beneficial effect upon the adhesive properties of the natural marine mussel adhesive.

The first event in the sequence of events resulting in the formation of a adhesive bond is believed to be simple adsorption or absorption or chemisorption. Subsequent events are chemical in nature and may involve crosslinking or other chemical mechanisms which increase the molecular weight of the natural adhesive material. Crosslinking also increases the cohesivehess of the adhesive material. All of these adhesive events —physical sorption, chemisorption, crosslinking, etc.—must take place in an aquatic environment in order to be useful to any mussel species. Many synthetic adhesives (particularly those built up in situ by polymerization from small monomers) are not very resistant to the subversive effects of water. The monomer can become diluted by water and may even have to compete with water in reactions involving active hydrogen or the like, Biological adhesives, being polypeptides adsorb water very vigorously but are competitive with water in any curing reactions which they undergo. Their high molecular weight enables them to resist dilution by water (notwithstanding their hydrophilic character), and the biological adhesive molecules have a certain degree of cohesiveness even before curing begins.

Despite all the advances in the understanding of the adhesive mechanisms utilized by marine mussels, it is still difficult to establish adhesive structure/function relationships in these large protein molecules. Some of the amino acid residues in the repeating amino acid sequences may contribute to the essentially random coil conformation of the protein in solution, and individual amino acid residues (such as DOPA) may provide curing sites or chelation sites for transition metal compounds in the environment. A complete study of the relationship between amino acid residues (individually or in sequence) and the adhesive function or other function of these residues or sequences is still in its infancy, and there are few rules or principles to guide researchers. Many protein adhesives remain to be characterized, and even for those already characterized, many comparisons between the structure of the protein and the particular requirements for adhesion need to be carried out. The advantages of biological adhesion have only recently begun to be appreciated in significant fields of use such as medicine. Some of these advantages have already been touched upon earlier and include resistance to subversive effects of water or biological fluids, negligible or innocuous amounts of heat generated during curing, biodegradability (where a short-lived adhesive bond is desirable), compatibility with biological systems, and the like, In situations where long-term bonds are desired (e.g. in the repair of broken teeth), the biological adhesives of this invention can perform well here also, because dental tissue is much less aggressive and is less likely to attack the bond. At the other extreme, when the objective is to repair self-repairing tissue, the environment is sufficiently aggressive to degrade the adhesive after the self-repair is complete.

Bioadhesives of this invention are self-curing, but the rate of cure tends to be slow. Curing can be accelerated with suitable accelerating and/or crosslinking agents.

The reasons for the performance, polymerization, and adhesive bond longevity of adhesives of this invention (and also of prior art biological adhesives) are also unclear. As noted previously, the prevalence of phenolic side chains (of DOPA and tyrosine, for example) may be relevant to the outstanding performance in the presence of water. DOPA is only rarely encountered as a component of naturally occurring proteins, but all the mussel adhesives studied in depth seem to have considerable amounts of this amino acid in the protein structure. Adhesive bond strength of various polyphenolic protein mussel adhesives has been measured. On glass, the attachment plaques (the byssal threads themselves are collagenous and are quite different in structure from the plaques) exhibit a mean adhesive tensile strength of $10^6$ newton/m$^2$, although maximal values often exceed $10^7$ newton/m$^2$. The substance in the plaque mediating adhesion between the collagenous threads and the substrate is the polyphenolic protein, i.e. the protein having a significant percentage of DOPA and tyrosine residues. These adhesive tensile strength values are reported, inter alia, in J. H. Waite, *J. Boil. Chem.*, 258, 2911–2915 (1983). Waite also explains the significance of the phenolic pendent groups and theorizes that both DOPA and 3- or 4-hydroxyproline in the known biological adhesives are derived post-translationally from amino acid residues of lower hydroxyl content, i.e. tyrosine and proline. respectively. Additional theories regarding the significance of DOPA in adhesive proteins focus on its apparent ability to displace water irreversibly from a surface and its ability to be readily oxidized to o-quinones which undergo nucleophilic addition reactions with primary amines such as lysine. Waite, *J. Biol. Chem.*, 258, 2911 (1983) at page 2913.

THE NATURAL MODEL

The naturally-occurring adhesive protein which has provided a model for the polypeptides of this invention was obtained from the Atlantic ribbed mussel (*Geukensia demissa*). As noted previously, *G. demissa* commonly lives with at least two-thirds of its body buried in the mud of intertidal salt marshes. Large numbers of these mussels can be collected from the salt marshes. and the adhesive material can be extracted or otherwise recovered from the animals by a variety of techniques. In one technique, the adhesive is obtained from the distal third of the feet of the mussels in a form which has not yet fully cured to form an adhesive plaque. In this technique. various steps must be taken to separate the adhesive protein from other proteins which occur in the foot structure. The tips of the feet are homogenized in a blender, the homogenate is centrifuged, and protein is precipitated from the supernatant. The DOPA-rich proteins are separated from other proteins with the aid of dialysis, elution chromatography, ultrafiltration, and purification by further elution and by reversed-phase high performance liquid chromotography (HPLC).

Another technique takes advantage of the fact that in captivity, each ribbed mussel adds about four to eight new threads per day to its byssus, and these threads are tipped with adhesive plaques averaging about 1 mm in diameter, The plaques contain a dense, open trabeculated substance dispersed in an amorphous granular matrix. The denser element forms a continuous region of contact at the interface. Accordingly, mussels can be tethered with rubberbands over glass or Plexiglass plates in an open circulating marine aquarium, and with time, these mussels will deposit the byssal threads and adhesive plaques. The plaques can be harvested from the glass or Plexiglass surface by first removing the thread and then scraping off the plaques with a sharp edge. The plaques thus recovered can be ground up in an aqueous medium from which insoluble proteins can be separated by centrifuging. The supernatant can then be subjected to electrophoresis and Western blotting.

The adhesive protein from the mussels can be digested with a suitable collagenase enzyme. The digested protein can be electrophoresed on acid-urea gels.

STRUCTURE OF THE ATLANTIC RIBBED MUSSEL ADHESIVE

In the first extraction technique described above, wherein the precursor of a major adhesive protein of *Geukensia* (*Modiolus*) *demissa* was isolated in quantity from the foot of the mussel yielded a protein having an apparent molecular weight of 130,000 daltons and a pI of 8.1. This protein contains a high proportion of glycine, glutamic acid or glutamine, lysine, and DOPA residues. The sequence of tryptic peptides suggests a pattern of repeated motifs, such as sequences with an Gly-DOPA-Lys "tail" and an X-Gly-DOPA-"head" wherein X is threonine or alanine in octapeptides and glutamine-threonine in nonapeptides. In some cases a tyrosine residue is found in place of the DOPA. Residues connecting the "head" to the "tail" include valine (Val), leucine (Leu), aspartic acid (Asp) or serine (Ser) linked to proline (Pro) or hydroxyproline (Hyp) alanine (Ala) or leucine (Leu). In the "head" and "tail", the usual amino acid residue symbols are used; thus, Gly is glycine, Tyr is tyrosine, Lys is lysine, etc. A diagonal line, e.g. DOPA/Tyr (3,4-dihydroxyphenylalanine/tyrosine) indicates that either DOPA or Tyr can be found at this position at the sequence.

The presence of Pro-Gly and Hyp-Gly sequences and delta-hydroxylysine in the protein is reminiscent of classical collagens; however, the protein is not labile to clostridial collagenase. Unlike typical collagens, the Gly residues probably occur at every fourth or fifth position in this unusual octapeptide or nonapeptide sequence.

The amino acid composition described above is somewhat similar to that of *M. edulis* and *M. californianus* in containing high levels of DOPA and lysine. However, two of the most abundant amino acids in the Atlantic ribbed mussel protein, Gly (20%) and Gln/Glu (14%) are only poorly represented in the protein from the other mytilids. The amount of hydroxyproline found in the Atlantic ribbed mussel adhesive (2%) is at a much lower level than was found in the other two mytilid species. Digestion of the Atlantic ribbed mussel adhesive protein with trypsin produced only three peaks on LH Sephadex; the first peak is trypsin, the second contains DOPA but was not further characterized, and the third of these peaks can be resolved into a great many DOPA-containing peptides by $C_8$ reversed phase HPLC. Many of these resemble the protein in their compositions. One of these is a tripeptide with the sequence Gly-DOPA-Lys; the others are closely related octa- and nonapeptides which include the tripeptide sequence or the less hydroxylated version of it, Gly-Tyr-Lys. The octapeptides can be represented as follows:

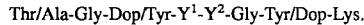

Thr/Ala-Gly-Dop/Tyr-$Y^1$-$Y^2$-Gly-Tyr/Dop-Lys.

In the foregoing formula, the three-letter symbols for amino acid residues have the usual meaning (Thr for threonine, Ala for alanine, Gly for glycine, Dop for dihydroxyphenylalanine, Tyr for tryosine, and Lys for lysine). The diagonal line indicates alternative residues (e.g. Thr or Ala, Dop or Tyr, etc.). The residue designated $Y^1$ is generally valine (Val), leucine (Leu), aspartic acid (Asp), or serine (Ser). The $Y^2$ residue is generally alanine (Ala), proline (Pro), hydroxyproline (Hyp), or leucine (Leu).

The nonapeptides include the above-described octapeptide structure with one additional residue for the N-terminus. (The Lys of the -Gly-Tyr/Dop-Lys "tail" provides the C-terminus as well as a pendent aliphatic amine group.) This N-terminus residue of the nonapeptide is typically glutamine (Gln) or, less frequently, glutamic acid (Glu).

Thus, the tripeptide "tail" and the (Gln)-Thr/Ala-Gly-Dop/Tyr- sequence of the octapeptides and nonapeptides are much less subject to variation than the two residues interposed between the "head" sequence and the "tail" sequence. The most prevalent $Y^1$-$Y^2$ combinations are Ser-Ala, a mixture of Val-Pro and Val-Hyp, a mixture of Val-Leu and Asp-Pro and a mixture of Val-Pro and Leu-Pro with a trace of Leu-Hyp.

Structure/activity relationships are by no means firmly established, but presently available data indicate that the tripeptide "tail" (Gly-Tyr/Dop-Lys) is present in the adhesive plaques and is associated with adhesive properties. Similarly, the three (in the case of octapeptides) or four (in the case of nonapeptides) residues at the "head" of the octapeptide or nonapeptide sequence are believed to have some relationship to adhesive properties, due, at least in part, to the pendent phenolic group provided by DOPA or Tyr. Because mature byssal adhesive plaques of mussels comprise proteins that are progressively crosslinked by quinone-tanning, it is believed that the chemical mechanism of at least one of these crosslinking reactions involves enzymatic oxidation of adjacent aromatic hydroxyl groups to orthoquinones (at least as a first step). See Waite, *J. Mar. Biol. Ass. UK* 65, 359–371 (1986) and *J. Comp. Physiol.* 156B, 491–496 (1986). Accordingly, it appears to be desirable that the tyrosine residues are hydroxylated to DOPA with a great frequence of occurrence in the polypeptide structures. Both phenol and o-dihydroxyphenol rings can of course be reacted with crosslinkers or with aldehydes (by the usual phenol/aldehyde reaction), but the natural crosslinking mechanism seems to relate more closely to DOPA than to Tyr.

Freshly secreted plaques appear to be less crosslinked than mature plaques, since significant protein is extractable from the former with 0.8M acetic acid and 8M urea. Although this invention is not bound by any theory, it is presently believed that a protein precursor for the plaque is produced and stockpiled in the foot of the Atlantic ribbed mussel. In immunoassay studies with antibodies, it was found that anti-Gdp cross-reacts with acid-urea extracts of the plaque, suggesting that some form of the DOPA-containing adhesive protein is present in the plaque.

Additional theorizing regarding structure/activity relationships can be based upon other known water-resistant polypeptide adhesives, e.g. the decapeptides disclosed in U.S. Pat. No. 4,585,585. However, analogies between the various natural models for polypeptide adhesives are somewhat limited. The differences between the tripeptide, octapeptide, and nonapeptide adhesives of this invention and the decapeptides of U.S. Patent No. 4,585,585 are greater than the similarities. Both the adhesive precursor of this invention and the known adhesives obtained from *M. edulis* and *M. californianus* can be said to be moderately high in molecular weight (about 130,000), basic (isoelectric points are on the basic side, perhaps due to the great frequency of Lys residues), insoluble in sodium dodecylsulfate, and composed largely of repeated peptide sequences. The prior art decapeptide sequence and the nonapeptide, octapeptide, and tripeptide sequences of the present invention all exhibit a DOPA/Tyr-Lys pair of acid residues at the carboxy terminus, and three amino acid residues are interposed between this pair and a Tyr/DOPA unit (in the case of decapeptides, octapeptides, and nonapeptides). Two of these three interposed residues may be little more than spacers, but the residue attached to the DOPA/Tyr-Lys pair at the carboxy terminus appears to be of considerable importance and is a particularly striking point of difference between the sequences of this invention and the known decapeptide sequences. Although this invention is not bound by any theory, it is believed that the Gly residue of the tripeptide or the three-residue carboxy-terminus "tail" of the octapeptides and nonapeptides imparts some of the features of collagen to the polypeptides of this invention. In the prior art decapeptides, the last three amino residues at the carboxy terminus are typically Ser/Thr-Tyr/DOPA-Lys. The tryptic peptide sequences obtained from the Atlantic ribbed mussel, on the other hand, exhibit a tripeptide "tail" which differs from the known sequence in two respects. First, there is less variability. The residue preceding Tyr/DOPA-Lys is consistently glycine (Gly), with essentially no detectable variation. Second, the presence of Gly at this position in the sequence is the second of two Gly residues in the nonapeptide and octapeptide sequences, so that Gly probably occurs at every fourth or fifth residue in the naturally-occurring sequences. The most characteristic of the decapeptide sequences obtained from the other two mytilid species appears to contain no glycine residues whatever. The greater occurrence of glycine residues is reminiscent of classical collagens, albeit still different from classical collagens in that the occurrence of Gly does not reach the level of every third residue, nor does one observe any Gly-DOPA-Gly sequences as found in the egg shell precursor proteins of trematodes.

Another feature of collagens observed to a considerable degree in peptide sequences of this invention is the presence of Pro-Gly sequences. These sequences can be found when $Y^2$ preceding the tripeptide "tail" is proline. No Pro-Gly sequences are reported for the decapeptides of U.S. Pat. No. 4,585,585.

The high occurrence of glycine residues in the polypeptides of this invention is just one of various differences between these polypeptides and the polypeptide sequences observed in proteins obtained from the other two mytilid species. For example, the hydroxylation pattern in the Atlantic ribbed mussel adhesive precursor appears to be significantly different from that of the other mytilid species. In the latter, the Tyr-5 and Tyr-9 are converted to DOPA at 35 and 100% efficiencies, respectively; in the former, the efficiencies are reversed, especially when one Pro/Hyp is present in the sequence. Again, this invention is not bound by any theory, but it is believed that the tyrosyl hydroxylase enzymes in both mussels may shun Tyr when preceded by a beta-turn. The $Y^1$-$Y^2$-Gly sequence (e.g. Val-Pro-Gly) discussed previously may be of significance in this regard. The sequence X-Pro-Gly forms a beta-turn which serves as a specific recognition site for the prolylhydroxylase of collagen. When -Pro-Gly is hydroxylated, the result typically is 4-trans-hydroxyproline-Gly, and such sequences are in fact observed in the adhesive protein precursor of the Atlantic ribbed mussel.

Still another structural difference in the polypeptide sequences of this invention involves the surprising variability of $Y^1$ and $Y^2$, particularly as compared to the closest corresponding positions in the known decapeptide sequences. This variability suggests either that post-translational modification occurs in a "shotgun" fashion, or that the method of protein extraction and isolation does not select incompletely from fully processed protein. On the whole, however, the polypeptides of this invention have fewer post-translational modifications. They also have significantly less proline compared to the known decapeptide sequences, and a lower isoelectric point.

Because of changes which can take place during isolation and purification of adhesive obtained from plaques deposited by the Atlantic ribbed mussel or from the stored adhesive precursor in the feet of this mussel, the polypeptide sequences of this invention do not exist precisely. as such in nature; however, they are believed to incorporate the important structural features of the natural proteins and are thus functionally similar to the natural model. For example, digestion with trypsin indicates (according to the literature) X-Lys-Gly sequences in the natural protein. Such sequences have yet to be demonstrated in any of the purified isolates obtained from Atlantic ribbed mussel adhesive protein. Moreover, substantial departures from the natural model can be undertaken without losing important aspects of the function of the naturally-occurring proteins. Even the tripeptide "tail" (Gly-Tyr/DOPA-Lys) is considered to have desirable self-curing (or chemically curable) properties by virtue of the phenolic ring of Tyr or, more preferably, the dihydroxyphenyl ring of DOPA. Indeed, it presently appears that the preferred tripeptide "tail" may have many of the desired properties of the entire octapeptide or nonapeptide or perhaps even the entire protein. Where biodegradability is desirable, the lysine at the carboxy terminus can be a significant point of attack for enzymes, provided that the lysine is not crosslinked through the pendent aliphatic amine group. (This aliphatic amine group is crosslinkable, both in natural mechanisms and in chemical mechanisms induced by addition of accelerators and/or crosslinkers.)

SYNTHETIC VARIATIONS OF THE NATURAL MODEL

As noted above, significant departures from the structure of the isolates are possible and can be very desirable from the standpoint of synthesis on an industrial scale. Although it cannot be determined with complete certainty which of the naturally occurring amino acid residues and/or sequences are adventitous and which are functional, it is nevertheless clear that polypeptides of this invention can be defined by the structural formulas set forth previously, particularly formulas I and II. Formula I is the tripeptide fragment which can be the carboxy-terminus "tail" of octapeptides and nonapeptides of formula II. Thus, the most fundamental amino acid sequence is the Gly-Tyr/DOPA-Lys "tail", and the next most fundamental sequence is the octapeptide which can be characterized as Thr/Ala-Gly-Dop/Tyr-$Y^1$-$Y^2$-, attached to the tripeptide "tail".

In totally synthetic versions of the polypeptides of this invention, the tripeptide can be a fundamental repeating unit, the nonapeptide or octapeptide can be a repeating unit, and various combinations of these units can be used. For example, the Thr/Ala-Gly-Dop/Tyr-$Y^1$-$Y^2$- fragment can be extended linearily to more than one (e.g. 10 to 20—and even up to 1000) units independently of the tripeptide fragment. Stated another way, the tripeptide fragment or the octapeptide sequence or the nonapeptide sequence can be the "monomer" of a "homopolymer" or the "co-monomer" of a "heteropolymer". Both random and block co-polymerization is contemplated, so that the fundamental sequences can be mixed or put into a set sequence and joined head/tail. Examples of non-random heteropolymers would be [tripeptide-octapeptide], [tripeptide-nonapeptide], [octapeptide-nonapeptide], [octapeptide-nonapeptide-tripeptide], and the like. The five or six-residue "head" of the octapeptide or nonapeptide, respectively, can, as indicated earlier, be independently chain-extended, but it is presently believed that this fragment is preferably combined with at least some of the tripeptide.

To produce a polypeptide adhesive on a commercial scale by total synthesis, it is desirable that the fundamental repeating unit of the linear chain be reasonably simple. However, even here variations are contemplated. Once a chain of eight or nine (or sixteen or eighteen, etc.) of amino acid residues has been built up, the molecular weight will increase rapidly with eachrepetition of the fundamental unit. Accordingly, only a few head/tail condensations of the fundamental unit will be needed to obtain a high molecular weight curable molecule. Conversely, many more head/tail condensations of tripeptide would be needed to provide a high molecular weight curable molecule, but the synthesis of the tripeptide fundamental unit is considerably easier than the total synthesis of, say, an eighteen-residue unit. In either event, it is not necessary to provide more than 100 repeats of the fundamental unit to obtain a highly useful precursor modeled on the natural precursor. Indeed, less than 50 repeats will be sufficient for most purposes, and economic considerations will normally limit the number of repeats to 10 or 20.

The fundamental unit can have a molecular weight as low as 300–400 daltons or, at the higher end, 1000–1500 daltons, or some multiple of these values. With head/tail condensation of several fundamental units, the adhesive precursor can have a molecular weight as high as about 20,000 or 50,000 daltons, the much higher molecular weights of the naturally-occurring precursors (which are well over 100,000 daltons) being unnecessary and moreover poorly suited to manufacture on a commercial scale.

The art of polycondensation of peptides is well developed. These condensations are carried out using peptides with either blocked or unblocked side chains. For example, it may be desirable to block the aliphatic primary amino side chain of the lysine residues so that chain extension will be strictly linear. These amino side chains can be blocked with N-alpha-t-butyloxycarbonyl ("BOC"). Similarly, it may be necessary or desirable to block the N-terminus. The C-terminus and pendent carboxyl groups (e.g. the —$C_2H_4COOH$ of glutaminic acid) can be blocked with a para-nitrophenylester. When it comes time to restore the amino and carboxyl functional groups, the BOC can be removed by treatment with 0.75M hydrochloric acid in dioxane, producing an amine hydrochloride salt. Similarly, the nitrophenyl ester blocking group can be removed by hydrolysis.

Condensation polymerization is achieved by forming the peptide salt and dissolving it in dry dimethylformamide (2.5 parts by weight) to which is added 0.22 parts by weight of triethylamine under stirring. The condensation polymer is precipitated during stirring.

CURING MECHANISM AND ADDITIVES

A major drawback of most synthetic adhesives is that they normally should be applied to dry surfaces in order to effect a strong bond, Indeed, the vast majority of adhesives bond dry surfaces more strongly than the same surfaces when wet. Even the water-resistant adhesives such as the various types of phenol-aldehyde or resorcinol-aldehyde polymers are not truly waterproof until after curing. The monomers are typically mixed, set, and cured at 10–50% relative humidity with no liquid water present, since liquid water and even excessive atmospheric humidity can interfere with curing. Water competes with the adhesive for surface area on which to bind and/or may hydrolyze or plasticize the adhesive. Polyphenolic polypeptide adhesives and adhesive precursors, on the other hand, are characterized by a very low aqueous dispersive effect, a low solubilty in neutral or slightly basic media, an ability to bind to tissue or other biological surfaces, and an ability to cure in the presence of liquid water—even under water, if desired.

As noted previously, the natural curing mechanism is believed to involve the formation of crosslinks by quinone-tanning. It appears that enzymatic oxidation of the DOPA residues to ortho-quinones can be the first step in the curing mechanism. Enzymes which can be utilized in this curing mechanism (or in other curing mechanisms) can be either or both of two basic types: the type which becomes a part of the cured (crosslinked) molecule, thereby adding its own molecular weight to the total molecular weight, and the type which acts more or less as a true catalyst and does not become integrated into the cured structure or is regenerated from it in free form.

Various conventional chemical curing mechanisms are useful in the context of this invention, including mechanisms which utilize active hydrogen, phenol/aldehyde reactions, condensation (e.g. amide-forming) reactions, and the like. For purposes of this disclosure "active hydrogen" is defined in accordance with the Zerewitinoff test in which methane is formed from the reaction between the H-containing molecule and a suitable Grignard reagent. The Zerewitinoff test is well known in the art. It was first used as early as 1912 and has been elaborated upon by others, particularly Kohler. An enormous variety of bifunctional or other polyfunctional compounds are reactive with active hydrogen.

In most of these curing mechanisms, the result is a complex 3-dimensional structure which is both cohesive in itself and is capable of providing a strong adhesive bond to the substrate. Bonds useful in tissue and cell culture, in surgery and in dental applications can be formed. When biodegradability is desirable, the 3-dimensionally structure, though bulky and complicated, is not totally immune to attack by enzyme systems in microorganisms prevalent in the environment. However, for maximum biocompatibility and biodegradability, the amino acid residues should be largely or even predominantly of the naturally occurring L-configuration.

Bifunctional crosslinking agents can, if desired, be amino acids or diamines or dicarboxylic acids. (These linking groups can also be used in linear chain extension of the fundamental repeating unit, in which case amino acids other than those discussed previously may be introduced into the molecule; examples of such amino acids include ornithine, homocysteine, citrulline, 3-aminotryosine, and the like, or readily available oligopeptides such as Ala-Cys-Ala, [Ala-Lys]$_3$, and the like.) In medical uses, it is generally preferable to use crosslinking agents which are relatively high in molecular weight in so that they will have less of a tendency to migrate from the site of adhesive application, thereby causing adventitious crosslinks. Similarly, if an accelerator is used, it is particularly preferred that it be a complex molecule (such an enzyme) and/or that it become integrated into the 3-dimensional structure resulting from the curing reactions. Suitable accelerators include those which catalyze the oxidation of an ortho-dihydroxyphenyl ring to an ortho-quinone.

In an industrial context, the molecular weight of the crosslinking agent and/or accelerator is a matter of less concern. Moroever, the rate of the curing reaction may have to be tailored to specific industrial applications. An important class of industrially useful agents is referred to in U.S. Pat. No. 4,585,585 as "bifunctional spacers". In these bifunctional compounds, the two functional groups are typically the same, hence they provide a means for linking like functional groups (e.g. linking a first pendent primary amino group to a second primary amino group or the like).

This class of "bifunctional spacers" can be further subdivided into groups reactive with active hydrogen (diisocyanates, di-epoxides, dihalides—particularly dichlorides—capable of condensation reactions with splitting off of a hydrogen halide, acid halides being typical of such compounds, etc.), compounds having functional groups reactive with carboxylic acids, compounds with functional groups capable of reacting with phenolic rings (e.g. dialdehydes), aryl dihalides, di-imido esters, and the like.

The dialdehydes may be of the type: OCH-R-CHO, wherein R is selected from the group comprising lower alkyl, aryl or substituted aryl, examples of suitable dialdehydes include glutaraldehyde, malonaldehyde, glyoxal, 1,4- butanedialdehyde, and the like. Useful imido esters comprise:

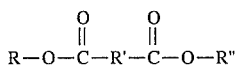

wherein R, R' and R" are independently selected from the group comprising lower alkyl, aryl or substituted aryl. Examples of suitable imido esters include dimethyl malonimidate, dimethyl suberimidate and dimethyl adipimidate.

Useful diisocyanates comprise: OCN-R-CNO wherein R is selected from the group comprising lower alkylene, arylene (including substituted arylene and polynuclear arylene) and difunctional cycloaliphatic residues (as in the case of isophorone diisocyanate). Examples of suitable diisocyanates include pentamethylene diisocyanate, hexamethylene diiosocyanate, heptamethylenediisocyanate, and toluene 2,4-and/or 2,6-diisocyanate. Useful aryl dihalides comprise:

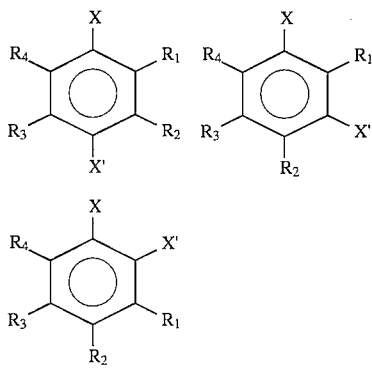

wherein X and X' are independently selected from the group comprising F, Cl, Br, and I and $R_1$, $R_2$ $R_3$, and $R_4$ are selected independently from the group comprising lower alkyl, aryl or substituted aryl. Examples of suitable aryl dihalides include p-dibromobenzene, o-bromoiodobenzene2,4-dibromotoluene and the like. Useful alkyl dihalides comprise: X-R-X', wherein X and X' may be independently selected from the group comprising F, Cl, Br and I; and R may be the residue of an alkyl or substituted alkyl group. Examples of alkyl dihalides include 1,2-dibromoethane, 1,3-dibromopropane, methylene bromide, methylene iodide and the like.

Dimaleimides which may be used comprise:

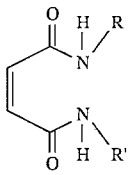

wherein R and $R_1$ are independently selected from the group comprising hydrogen, lower alkyl or aryl. Examples of suitable dimaleimides include bis(N-maleimidomethyl)ether and the like.

These bifunctional compounds will provide an adequate crosslink density for a wide variety of industrial uses and medical uses as well. If unusually high crosslink densities are required, crosslinkers of even greater functionality can be employed, e.g. triisocyanates such as the reaction product of toluene diisocyanate and trimethylolpropane. (An essentially completely isocyanate-capped crosslinker can be obtained by reacting the diisocyanate and the triol in an NCO/OH ratio of at least about 2:1.) An interesting capability of the isocyanates is that they can react both with free amino groups and free carboxylic acid groups.

GRAFT OR OTHER CO-POLYMERIZED RELATIONSHIPS WITH SYNTHETIC NON-PEPTIDE POLYMERS

If desired, polypeptides of this invention can be chemically combined with non-peptide polymers, most typically by grafting them on to a synthetic polymer backbone having pendent carboxyl groups and/or pendent amino groups or the like. Bifunctional agents such as diisocyanates can be used to link an N-terminus or C-terminus of the polypeptide to a like group (COOH or $NH_2$) of the synthetic polymer. It is not absolutely essential that the site of attachment on the synthetic polymer be a repeating functional group, although repeating functional groups are preferred. It is also not essential that the repeating functional group of a synthetic polymer backbone be pendent from the chain; the site of attachment can be part of the chain, as in the case of nylon-2 or a poly (alkyleneimine). The secondary amino groups in the chain of a poly(alkyleneimine) are reasonably reactive toward bifunctional linking agents such as diisocyanates.

The presently preferred synthetic polymer backbone is one which contains acrylic acid or methacrylic acid units. The pendent carboxyl groups can be linked to polypeptides of this invention in a conventional manner through the Lys residue or the N-terminus at the "head" of an octapeptide or nonapeptide, e.g. through the free primary amino group of a terminal glutamine residue. Thus, a particularly preferred graft co-polymer of this invention has the following formula

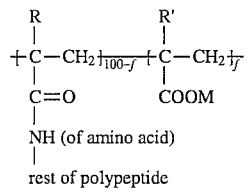

where R and R' are the same or different and are

H or lower alkyl (e.g. methyl)

M is H or an alkali metal, f is zero or a number from 1 to 99.

APPLICATIONS OF BIOADHESIVE TECHNOLOGY

As is known in the art, bioadhesive polyphenolic polypeptides are of considerable interest in the field of medicine. These polypeptides, even when made up of only a few amino acid residues, can be used as building blocks in the construction of larger polyphenolic molecules having the adhesive capabilities of the natural bioadhesive protein which serves as the model for their structure. The low molecular weight precursors thus serve as "monomers" or prepolymers which are capable of being cured by one of the curing mechanisms described previously. The cured materials behave as high polymers and adhere to teeth and bone surfaces as well as to softer tissue. The presence of water or biological fluids does not prevent curing. The polypeptide structure absorbs water well but are not diluted by water. The chemical curing reactions compete well with other reactions capable of taking place at the same time and in the same environment. This does not mean that these polypeptides are limited to medical uses. On the contrary, they can provide adhesive bonding to inanimate and inorganic surfaces, including surfaces of glass, iron, steel, slate, wood, etc. The resulting adhesive bonds can be durable in the presence of water for a period of years; however, amino acid residues in the cured polypeptide structure are not completely immune to attack by microorganisms, hence desirable levels of biodegradability can be achieved. Uncured polypeptide adhesive precursors of this invention typically have molecular weights on the order of 1000 to 50,000, more typically 1000–20,000 daltons. The use of these polypeptides is facilitated by formulating them as two-part systems. Part A is the adhesive precursor, and part B is an accelerator and/or a crosslinking agent. In medical practice, the preferred part B is a high molecular weight accelerator such as an enzyme for catalyzing oxidation reactions. In industrial practice, the part B can be a crosslinking agent such as a dialdehyde, diisocyanate, triisocyanate, or the like. The accelerator, in this context, can be a relatively simple molecule such as a conventional metal salt or organometallic catalyst, an acid or base catalyst, a Lewis acid catalyst ($BF_3$, etc.) or any other compound capably of overcoming kinetic barriers to the desired curing reaction or reactions. Surfaces can be adhered to each other by applying a polypeptide of this invention to one or both of the surfaces to be adhered, bringing the surfaces into contact, and then initiating the curing reaction or permitting a self-cure to take place. When the polypeptide of this invention is in the form of a relatively low molecular weight adhesive precursor, the precursor can be extended with inert materials or dissolved or suspended in liquid media which have no long term adverse effect upon the precursor structure.

In uses (particularly industrial uses) of a synthetic adhesive precursor of this invention wherein neither biocompatibility nor biodegradability is important, D-amino acids can be used in peptide monomers, even though they are not preferred. Otherwise, only L-amine acids should be used. When the adhesive precursor is bioengineered or obtained from a natural source, the natural L-configuration will of course prevail.

Although total or partial chemical or biochemical or bioengineered synthesis is preferred for making large quantities (e.g. several grams or more) of polypeptide adhesives of this invention, small quantities can be obtained from mussels in practical manners by purifying and stabilizing techniques such as extraction/borate complexing technique of U.S. Pat. No. 4,496,397 (Waite), issued Jan. 29, 1985. The preferred natural source of polyphenolic protein is distal portions of mussel feet, homogenized in a suitable medium and extracted with in acetic acid (e.g. 1–10 wt.-% aqueous acetic acid), as in the technique described in U.S. Pat. No. 4,496,397, except that the acetic acid medium is very ineffective unless it contains urea (e.g. 1 to 10 moles of urea per mole of acetic acid solution). After centrifuging, the protein precipitate from the supernatant is dialyzed against a large volume of borate solution at a pH of 7.0 to 9.0, much as in the technique of U.S. Pat. No. 4,496,397. A clear borate medium containing extracted polyphenolic protein can be concentrated and then purified by one or more elution chromatography steps. The acid-extracted protein from the mussel foot binds to sulfonylethyl-Sephadex and can be eluted at about 1.05M guanidine hydrochloride. Further elution can be carried out with a Sephadex column and 0.8M acetic acid and by reversed-phase high performance liquid chromatography (HPLC) using a $C_8$ column with an acetonitrile gradient in water, where both solvents contain trifluoroacetic acid, as reported in the scientific literature.

Trypsin can be added to purified protein at an enzyme-to-protein weight ratio of 1:100, and digestion of the protein can be conducted at normal ambient temperatures (e.g. 20°–25° C.) for 12 hours under nitrogen.

EXAMPLE

A polyphenolic protein from the distal third of feet of Atlantic ribbed mussels was extracted, purified, and digested as described above. Fractions absorbing ultraviolet light of 280 nm wavelength were freeze-dried and a portion was hydrolyzed in 6M HCl with 5 wt.-% phenol in vacuo at 110° C. for 24 hours. The amino acid composition of hydrolyzed peptides and proteins was determined us ing a single column Beckman 6300 Autoanalyzer. N-terminal amino acid sequence of tryptic peptides was determined by automated Edman degradation with the use of an Applied Biosystems ( Foster City, Calif.) model 470 A gas phase sequenator in accordance with J. Ozols, *J. Biol. Chem.* 261, 3965–3979 (1986).

Digestion of the polyphenolic protein with trypsin produced only three peaks on LH Sephadex; the first peak was trypsin, the second contains DOPA but was not further characterized. The third peak, which contained several DOPA-containing polypeptides, was resolved by $C_8$ reversed phase HPLC. Many of these polypeptides resemble the protein in their compositions. Twenty-one polypeptides ( arbitrarily designated "A" through "U") showed significant absorbance at 280 nm, and of these, the most prominent. absorbance peaks were peptides B, D, P, R and T. The amino acid residue sequences of these five peptides were as follows:

B Gly-Dop-Lys
D Thr-Gly-Dop-Ser-Ala-Gly-Dop-Lys
P Gln-Thr-Gly-Dop-Val-Pro-Gly-Dop-Lys
R Gln-Thr-Gly-Dop-Asp-Pro-Gly-Tyr-Lys
T Gln-Thr-Gly-Dop-Leu-Pro-Gly-Dop-Lys
(Gly=glycine, Dop=3,4-dihydroxyphenylalanine, Lys=lysine, Gln=glutamine, Thr=threonine, Ser=serine, Ala=alanine, Val=valine, Pro=proline, Asp=aspartic acid, Tyr=tyrosine, Leu=Leucine.)

These five peptides were selected as adhesive precursors. All are curable with enzymes which catalyze oxidation of the dihydroxyphenyl ring of Dop, particularly peptides B, D, R, and T.

What is claimed is:

1. An isolated and purified polypeptide containing at least one of the amino acid sequences set forth below:

(A) Gly-Dop-Lys (B) Thr-Gly-Dop-Ser-Ala-Gly-Dop-Lys (C) Gln-Thr-Gly-Dop-Val-Pro-Gly-Dop-Lys (D) Gln-Thr-Gly-Dop-Asp-Pro-Gly-Tyr-Lys (E) Gln-Thr-Gly-Dop-Leu-Pro-Gly-Dop-Lys wherein the above three-letter symbols are defined as follows:

Gly is a glycine residue,

Dop is a 3,4-dihydroxyphenylalanine residue,

Lys is a lysine residue,

Gln is a glutamine residue,

Thr is a threonine residue,

Ser is a serine residue,

Ala is an alanine residue,

Val is a valine residue,

Pro is a proline residue,

Asp is an aspartic acid residue,

Tyr is a tyrosine residue and

Leu is a leucine residue.

2. A synthetic tripepride, octapeptide, or nonapeptide, wherein the synthetic tripeptide has the sequence (I)

Gly-Dop/Tyr-Lys     (I)

the synthetic octapeptide has the formula (II)

Thr/Ala-Gly-Dop/Tyr-$Y^1$-$Y^2$-Gly-Tyr/Dop-Lys     (II)

and the synthetic nonapeptide has the formula (Ill)

[Gln/Glu-Thr/Ala-Gly-Dop/Tyr-$Y^1$-$Y^2$-Gly-Tyr/Dop-Lys     (III)

wherein the above three-letter symbols represent the following amino acid residues:

Gly is a glycine residue,

Dop is a 3,4-dihydroxyphenylalanine residue,

Lys is a lysine residue,

Gln is a glutamine residue,

Glu is a glutamic acid residue,

Hyp is a hydroxyproline residue, wherein the diagonal line indicates alternative amino acid residues, and wherein $Y^1$ represents the residues of valine, leucine, aspartic acid, or serine, and $Y^2$ repreeente the residues of alanins, proline, hydroxyproline, or leucine.

3. A synthetic homopolymer or random or block copolymer obtained by polymerizing, head/tail, up to about 50 tripeptides, octapeptides, or nonapeptides of the sequences (I), (II), and (III) of claim 2, whereby the total number of said sequences in the homopolymer or random or block copolymer does not exceed about 50.

4. A synthetic polymer consisting essentially of up to 50 head/tail polymerized tripeptides (I) of claim 2.

5. A synthetic polymer consisting essentially of up to 50 head/tail polymerized octapeptides (II) of claim 2.

6. A synthetic polymer consisting essentially of up to 50 head/tail polymerized nonapeptides (III) of claim 2.

7. A synthetic peptide of claim 2 having the sequence (A) Gly-Dop-Lys (B) Thr-Gly-Dop-Ser-Ala-Gly-Dop-Lys (C) Gln-Thr-Gly-Dop-Val-Pro-Gly-Dop-Lys (D) Gln-Thr-Gly-Dop-Asp-Pro-Gly-Tyr-Lys, or (E) Gln-Thr-Gly-Dop-Leu-Pro-Gly-Dop-Lys.

8. A synthetic tripeptide according to claim 2, said tripeptide having the sequence Gly-Dop-Lys.

9. A synthetic octapeptide according to claim 2, said octapeptide having the sequence Thr-Gly-Dop-Ser-Ala-Gly-Dop-Lys.

10. A crosslinked polypeptide which is the reaction product of the components comprising the synthetic homopolymer or random or block copolymer of claim 3, and a crosslinking agent.

11. A crosslinked polypeptide according claim 10, wherein said synthetic homopolymer or random or block copolymer is crosslinked through the phenolic groups of said Dop or Tyr or through both said phenolic groups and the pendent —$(CH_2—)_4NH_2$ groups of said Lys.

12. A polypeptide which has been isolated in substantially pure form from the dialyzed DOPA-rich protein or protein precursor stored in the foot of the Atlantic ribbed mussel or which has been isolated from the digested protein obtained from the adhesive protein of the Atlantic ribbed mussel and has been electrophoresed on an acid-urea gel, said polypeptide having the formula:

Thr/Ala-Gly-Dop/Tyr-$Y^1$-$Y^2$-Gly-Dop/Tyr-Lys or the formula:

Gln-Thr/Ala-Gly-Dop/Tyr-$Y^1$-$Y_2$-Gly-Dop/Tyr-Lys wherein the above three-letter symbols are defined as follows:

Gln=glutamine residue

Thr=threonine residue

Ala=alanine residue

Gly=glycine residue

Dop=3,4-dihydroxyphenylalanine residue

Tyr=tyrosine residue

Lys=lysine residue, and $Y^1$ and $Y^2$ represent the following amino acid residues:

$Y^1$=a serine, valine, aspartic acid, or leucine residue, and $Y^2$=an alanine, proline, hydroxyproline, or leucine residue, and wherein a diagonal mark indicates alternative residues and wherein either said polypeptide can recur up to 20 times.

\* \* \* \* \*